United States Patent
Brown et al.

(10) Patent No.: US 11,350,967 B2
(45) Date of Patent: Jun. 7, 2022

(54) APPARATUS INCLUDING A CYLINDRICAL BODY AND A NUB

(71) Applicants: Maureen Brown, Austin, TX (US); Marc Brown, Austin, TX (US)

(72) Inventors: Maureen Brown, Austin, TX (US); Marc Brown, Austin, TX (US)

(73) Assignee: Mosie LLC, Austin, TX (US)

(*) Notice: Subject to any disclaimer, the term of this patent is extended or adjusted under 35 U.S.C. 154(b) by 338 days.

(21) Appl. No.: 16/267,254

(22) Filed: Feb. 4, 2019

(65) Prior Publication Data
US 2021/0307784 A1    Oct. 7, 2021

Related U.S. Application Data

(63) Continuation-in-part of application No. 14/691,220, filed on Apr. 20, 2015, now abandoned, which is a continuation-in-part of application No. 14/272,368, filed on May 7, 2014, now Pat. No. 10,231,755.

(51) Int. Cl.
*A61M 5/178* (2006.01)
*A61B 17/43* (2006.01)
*A61M 5/315* (2006.01)

(52) U.S. Cl.
CPC ......... *A61B 17/43* (2013.01); *A61M 5/31576* (2013.01); *A61B 2560/04* (2013.01)

(58) Field of Classification Search
CPC ..... A61B 17/43; A61D 19/027; A61M 5/3134
See application file for complete search history.

(56) References Cited

U.S. PATENT DOCUMENTS

| | | | |
|---|---|---|---|
| 2,514,575 A | 11/1950 | Hein | |
| 2,688,968 A | 9/1954 | Pauli | |
| 3,721,229 A * | 3/1973 | Panzer | A61M 31/00 600/435 |
| 4,043,334 A | 8/1977 | Brown | |

(Continued)

FOREIGN PATENT DOCUMENTS

WO    WO2013038166 A1    3/2013

OTHER PUBLICATIONS

Abou-Setta, Intrauterine insemination catheters for assistedreproduction: a systematic review and meta-analysis, Human Reproduction vol. 21, No. 8 pp. 1961-1967, 2006.

(Continued)

*Primary Examiner* — Christine H Matthews
(74) *Attorney, Agent, or Firm* — Michael Best & Friedrich LLP

(57) ABSTRACT

An apparatus may include a plunger and a substantially cylindrical body. The substantially cylindrical body may include an end portion having rounded edges and may define a cavity sized to receive the plunger. The substantially cylindrical body may include at least one opening extending from the cavity to an external surface. The at least one opening may a substantially irregular shape. In some embodiments, the at least one opening may extend from the cavity through a nub to the external surface. The nub may have a rounded shape. In some embodiments, the substantially irregular shape may include one of a slit, an oval shape, an elliptical shape, an hourglass shape, a rectangular shape, and a diamond shape. In some embodiments, the opening may be part of a non-cylindrical fluid passage.

16 Claims, 14 Drawing Sheets

(56) References Cited

U.S. PATENT DOCUMENTS

| | | |
|---|---|---|
| 4,287,888 A | 9/1981 | Schwarz |
| 4,809,458 A | 3/1989 | Tanikuro et al. |
| 5,004,443 A | 4/1991 | Su |
| 5,084,004 A | 1/1992 | Ranoux |
| 5,147,315 A | 9/1992 | Weber |
| 5,259,836 A | 11/1993 | Thurmond |
| 5,266,071 A | 11/1993 | Elftman |
| 5,472,419 A | 12/1995 | Bacich |
| 5,496,272 A | 3/1996 | Chung |
| 5,531,709 A | 7/1996 | Eykmann et al. |
| 5,536,234 A | 7/1996 | Newman |
| D401,324 S | 11/1998 | Hjertman et al. |
| 5,858,354 A | 1/1999 | Brinster |
| D407,093 S | 3/1999 | Wells |
| 5,904,665 A | 5/1999 | Muharib |
| D412,206 S | 7/1999 | Basile et al. |
| 5,944,698 A | 8/1999 | Fischer et al. |
| 5,967,368 A | 10/1999 | Guillermier |
| D436,532 S | 1/2001 | Richardson |
| D439,010 S | 3/2001 | Sogaro |
| D445,176 S | 7/2001 | Landers |
| 6,264,638 B1 | 7/2001 | Contente |
| 6,551,236 B1 | 4/2003 | Liegois |
| 6,699,226 B2 | 3/2004 | Velazquez |
| 6,890,708 B2 | 5/2005 | Mattihijs-Rijsenbilt |
| 6,936,034 B2 | 8/2005 | Watkins |
| D515,736 S | 2/2006 | Angeletta |
| RE39,533 E | 3/2007 | Ranoux |
| D550,851 S | 9/2007 | Roehrig |
| 7,282,363 B1 | 10/2007 | Ranoux |
| 7,344,492 B2 | 3/2008 | Ainley |
| D574,954 S | 8/2008 | Smith |
| 7,419,465 B2 | 9/2008 | Ainley |
| 7,666,160 B2 | 2/2010 | Rajala |
| D618,347 S | 6/2010 | Bradshaw |
| 7,759,115 B2 | 7/2010 | Etheredge |
| 7,837,611 B2 | 11/2010 | Ainley |
| 8,323,178 B2 | 12/2012 | Ainley |
| 8,992,505 B2 | 3/2015 | Thorne, Jr. et al. |
| D726,028 S | 4/2015 | Thompson |
| D729,931 S | 5/2015 | Takeuchi et al. |
| D734,539 S | 7/2015 | Yeo |
| D739,524 S | 9/2015 | Zemel et al. |
| 9,146,144 B2 | 9/2015 | Hui et al. |
| D741,476 S | 10/2015 | Hiraoka et al. |
| D743,025 S | 11/2015 | Berler |
| D750,228 S | 2/2016 | Strong et al. |
| 9,968,769 B2 | 5/2018 | Sasayama et al. |
| D844,777 S | 4/2019 | Combes et al. |
| D852,360 S | 6/2019 | Lund |
| D861,895 S | 10/2019 | Clores |
| D866,248 S | 11/2019 | Baron et al. |
| 2002/0198498 A1 | 12/2002 | Porat et al. |
| 2004/0006291 A1 | 1/2004 | Rehrig |
| 2006/0074273 A1 | 4/2006 | Smith |
| 2006/0122563 A1 | 6/2006 | Ziv |
| 2008/0078408 A1* | 4/2008 | Park .................. A61K 33/38 128/830 |
| 2008/0161752 A1* | 7/2008 | Rajala ................ A61M 31/00 604/48 |
| 2009/0326479 A1 | 12/2009 | Janish |
| 2011/0034868 A1 | 2/2011 | Eichhorst et al. |
| 2011/0224648 A1 | 9/2011 | Secci |
| 2013/0090629 A1 | 4/2013 | Cant |
| 2013/0217961 A1 | 8/2013 | Godden |
| 2014/0046127 A1 | 2/2014 | Topolovac |
| 2014/0107410 A1 | 4/2014 | Rosenberg |
| 2014/0309488 A1 | 10/2014 | Fowler |
| 2014/0367409 A1 | 12/2014 | Digregorio et al. |

OTHER PUBLICATIONS

Search Report and Written Opinion, PCT/US2015/029310, dated Aug. 27, 2015, 7 pages.

Suarez, Sperm Transport in the Female Reproductive Tract, Human Reproduction Update, vol. 12, No. 1 pp. 23-37, 2006.

* cited by examiner

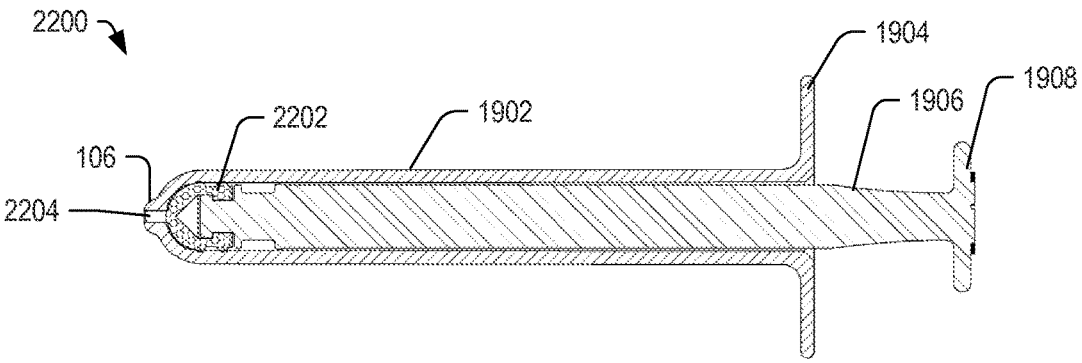
FIG. 22A
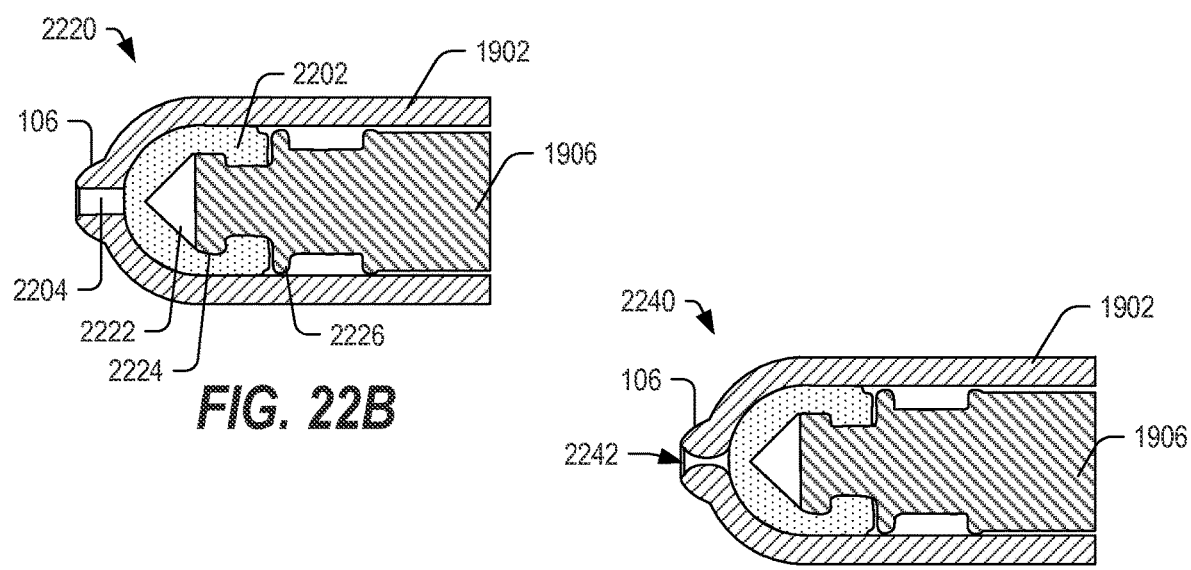
FIG. 22B
FIG. 22C
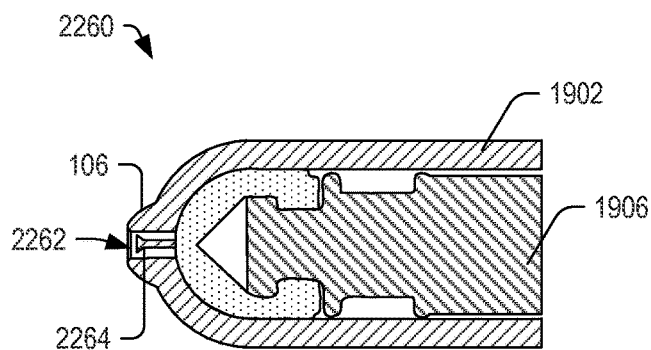
FIG. 22D

APPARATUS INCLUDING A CYLINDRICAL BODY AND A NUB

CROSS-REFERENCE TO RELATED APPLICATION(S)

This application claims priority to and is a continuation-in-part application of co-pending U.S. patent application Ser. No. 14/272,368 filed on May 7, 2014 and entitled "Apparatus Including a Cylindrical Body and a Nub", and Ser. No. 14/691,220 Filed Apr. 20, 2015, and also entitled "Apparatus Including a Cylindrical Body and a Nub," both of which applications are incorporated by reference herein in their entirety.

FIELD

The present disclosure is generally related to a fluid dispensing apparatus, and more particularly to an apparatus including a substantially cylindrical body and a nub, where the cylindrical body and the nub are rounded.

BACKGROUND

Infertility is a common problem among couples. An evaluation by a doctor is often recommended after a period of time (such as one year) of unprotected intercourse without achieving conception. While it is sometimes possible to identify correctable issues that may be preventing conception, some couples pursue expensive medical solutions, such as in vitro fertilization at a fertility clinic. A personal insemination syringe for home use provides an effective and affordable alternative to expensive and complicated medical procedures.

SUMMARY

In an embodiment, an apparatus may include a substantially cylindrical body including an end portion having rounded edges and at least one opening. The apparatus further may include a nub extending from the end portion proximate to the at least one opening. The nub may include a substantially rounded end. In some embodiments, the opening may have an irregular shape, an oval or elliptical shape, an hour-glass shape, a diamond shape, or another shape. In some embodiments, the opening may define or couple to a non-cylindrical fluid passage.

In still another embodiment, an apparatus may include a tubular element including a body portion and a distal end and including a substantially smooth surface having rounded edges. The apparatus further may include a nub having an opening. In some embodiments, the apparatus may further include one or more second openings distributed about the nub. In some embodiments, at least one of the opening and the one or more second openings may have an irregular shape. In some embodiments, the opening may be configured to diffuse a fluid dispelled through the opening.

In some embodiments, an apparatus may include a tubular element including a body portion defining an internal cavity and including a distal end. The distal end may include a nub and an opening having a non-circular shape. The tubular element may include a substantially smooth exterior surface having rounded edges. The apparatus may further include a plunger configured to fit within the cavity.

BRIEF DESCRIPTION OF THE DRAWINGS

FIGS. 22A-22D are front views of the syringe of FIG. 19A, in accordance with certain embodiments of the present disclosure.

DETAILED DESCRIPTION OF ILLUSTRATIVE EMBODIMENTS

In the following discussion, the same reference numbers are used in the various embodiments to indicate the same or similar elements. Embodiments of an apparatus are disclosed below that include a substantially cylindrical body portion and a nub that extends from a distal end of the body portion. The cylindrical body portion may be a syringe, a sheath sized to receive a syringe, or cap configured to couple to a syringe. The nub may have a rounded shape, such as a hemispherical shape, a ring shape (with rounded edges), an elliptical shape (with rounded edges), a bulbous shape, or some other rounded shape. In some embodiments, the nub may have a diameter that is less than a cross-sectional diameter of the syringe. Further, the edges of the syringe, the sheath, the cap, or any combination thereof, may be rounded, presenting a smooth transition from the elongate body portion to the distal end. In some embodiments, portions of the syringe, portions of the cap, portions of the sheath, or any combination thereof may be formed from a first material, while other portions of the syringe, the sheath, the cap, the nub, or any combination thereof may be formed from a second material. In some embodiments, the second material may be more flexible or malleable than the first material.

In some embodiments, the apparatus may be used for artificial insemination by filling a fluid canal of a barrel of the syringe with seminal fluid, and by inserting the apparatus into the vaginal canal to deliver seminal fluid through the vaginal canal to the cervix of the woman. The nub may provide tactile feedback to the woman by allowing her to feel when the distal end of the apparatus is touching the cervix. Further, the feedback provided by the nub may allow the woman to adjust the position of the apparatus relative to the cervix prior to depression of the plunger of the syringe to deliver the seminal fluid. Embodiments of the apparatus are described below with respect to FIGS. 1-13.

Figure 1:
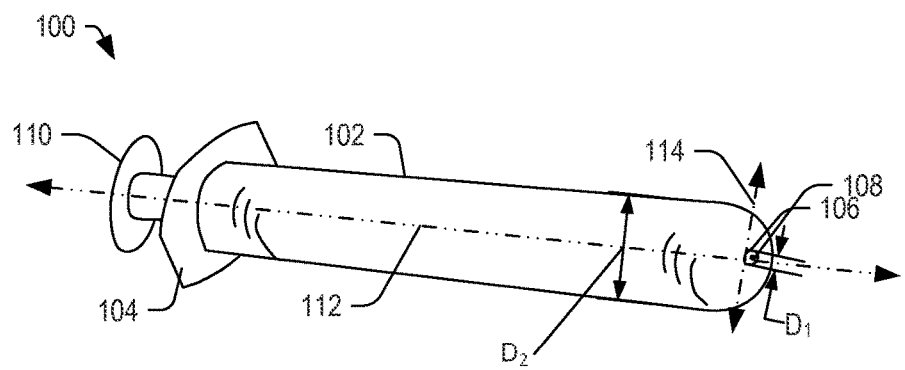
FIG. 1 is a perspective view of an apparatus including a syringe with a nub, in accordance with certain embodiments of the present disclosure.

FIG. 1 is a perspective view of an apparatus 100 including a syringe 102 with a nub 106 according to some embodiments. The syringe 102 may include a body having a proximal end with a flange 104 and may define a cavity sized to receive a plunger 110 to draw fluid into the cavity and to propel fluid through the opening 108. The flange 104 may be used as leverage by a user when depressing the plunger 110. Further, the body of the syringe 102 may include a distal end with the nub 106. The distal end of the body of the syringe 102 may also include an opening 108 to allow fluid flow. In the illustrated example, the opening 108 extends through a corresponding opening in the nub 106; however, the nub 106 and the opening 108 may be offset from one another. In some embodiments, the opening 108 may be offset from a center of the distal end of the syringe 102. In some embodiments, the nub 106 may be offset from the center of the distal end.

In some embodiments, the nub 106 and the opening 108 may be offset from the center of the distal end.

In some embodiments, the body of the syringe 102 may have a substantially cylindrical shape (or tubular shape) forming a fluid conduit and having rounded edges at the distal end. Further, the nub 106 may have a substantially semi-spherical shape and may extend outward from the distal end of the syringe 102 proximate to a longitudinal axis 112 of the syringe 102. In some embodiments, the nub 106 may have a diameter (D1) that is orthogonal to the longitudinal axis 112 of the syringe 102 and that is smaller than a diameter (D2) of the body of the syringe 102. In some embodiments, the body of the syringe 102 may be formed from a first material, and the nub 106 may be formed from a second material. In some embodiments, the body of the syringe 102 and the nub 106 may be formed from a unitary piece of material (such as molded antibacterial plastic).

In some embodiments, a user may draw fluid into a cavity within the body of the syringe 102 by pulling the plunger 110. The user may then insert the syringe 102 into the vaginal cavity and depress the plunger 110 to dispense the fluid through opening 108. The nub 106 may provide feed feedback to the woman to allow her to feel the position of the distal end of the syringe 102 against her cervix prior to dispensing the fluid.

In some embodiments, the rounded edges of the distal end of the body of the syringe 102 and the rounded shape of the nub 106 provide a substantially smooth and relatively comfortable feel as compared to a standard syringe that has corners and a pointed (though needle-less) end. While a conventional syringe may have edges or corners that can be sharp or abrasive, the syringe 102 and the nub 106 are rounded to provide smooth edges.

While the illustrated example of FIG. 1 included a single opening that extends through the nub 106, it should be understood that the distal end of the syringe 102 may include one or more openings to allow fluid passage to and from the cavity within the body of the syringe 102 and the outside environment. One possible example of a syringe that may include multiple openings is described below with respect to FIG. 2.

Figure 2:
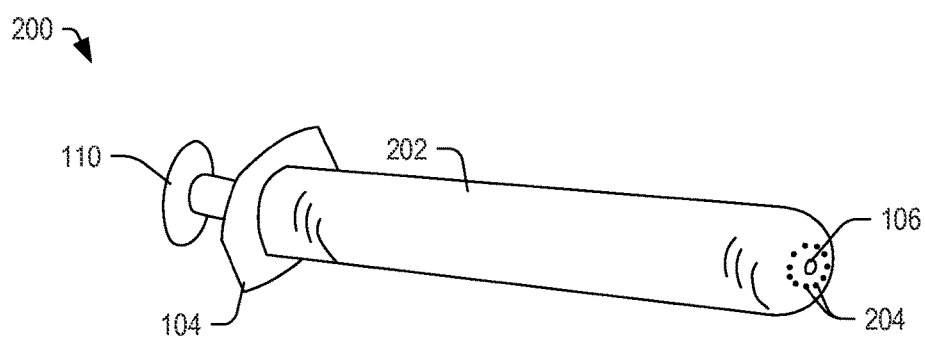
FIG. 2 is a perspective view of an apparatus including a syringe with a nub, in accordance with certain embodiments of the present disclosure.

FIG. 2 is a perspective view of an apparatus 200 including a syringe 202 with a nub 106 according to some embodiments. The syringe 202 may include the flange 104 and may include a cavity sized to receive the plunger 110. The syringe 202 further may include multiple openings 204 extending from the cavity to the outside environment. In the illustrated example, the openings 204 are distributed about the nub 106 and are offset from the nub 106. In some embodiments, additional openings 204 or fewer openings may be provided. In some embodiments, the openings 204 may be distributed circumferentially along the sidewalls of the body of the syringe 202 near the distal end. Further, in some embodiments, the openings 204 may align with corresponding openings that extend through the nub 106.

In the illustrated examples of FIGS. 1 and 2, the syringe 102 and 202 may be formed from a first material, such as a substantially rigid, anti-bacterial and anti-microbial plastic material, while the nub 106 may be formed from a second material, that may also have anti-bacterial and anti-microbial properties, but that may be more elastic or malleable than the first material. Additionally, in some embodiments, the nub 106 may be attached to or coupled to the syringe 102,202. In some embodiments, the nub 106 may be integrally formed with the syringe 102, 202. An example of some embodiments of the syringe 202 having an integrally formed nub 106 and including the opening 108 is described below with respect to FIG. 3.

Figure 3:
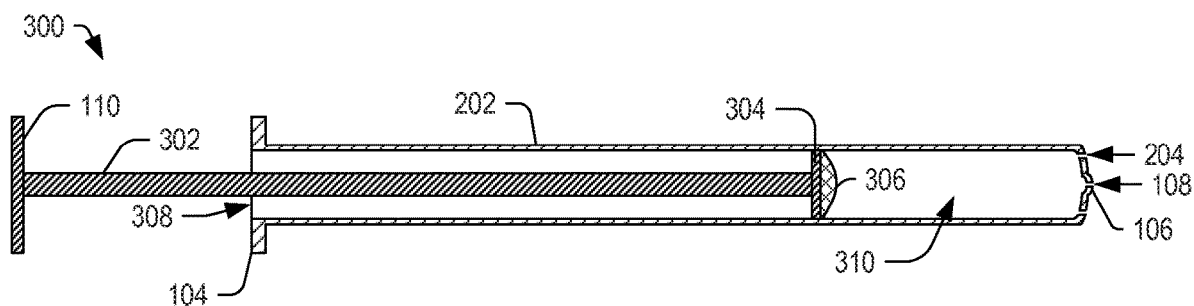
FIG. 3 is a cross-sectional view of an apparatus including a syringe with a nub, in accordance with certain embodiments of the present disclosure.

FIG. 3 is a cross-sectional view of an apparatus 300 including a syringe 202 with a nub 106 according to some embodiments. The syringe 202 may include a body portion that defines a cavity 308 that extends from a proximal end, which may include the flange 104, to a distal end, which may include openings 204, and the nub 106. Additionally, in some embodiments, the nub 106 also may include an opening 108. The openings 108 and 204 extend through the distal end of the body of the syringe 202 to permit fluid flow between a fluid area 310 and the environment.

The apparatus 300 further may include the plunger 110 including a rod portion 302 and an end portion 304. A gasket or seal 306 may be coupled to the end portion 304 to provide a fluid seal to prevent fluid flow from the fluid area 310 toward the body portion 302 and to draw fluid through the openings 108 and 204 in to the fluid area 310 or to drive fluid from the fluid area 310 through the openings 108 and 204.

In some embodiments, the nub 106 may be part of the distal end of the body of the syringe 202. In some embodiments, the nub 106 may omit the opening 108 and the openings 204 may be included. In some embodiments, the openings 204 may be omitted and the opening 108 may be included.

In some embodiments, an outer sheath or covering may be provided that may be adapted to cover a needle-less syringe. The outer sheath may be configured to receive the syringe and to provide a rounded distal end and a nub. An example of an apparatus including a sheath is described below with respect to FIGS. 4-10 according to some embodiments.

Figure 4:
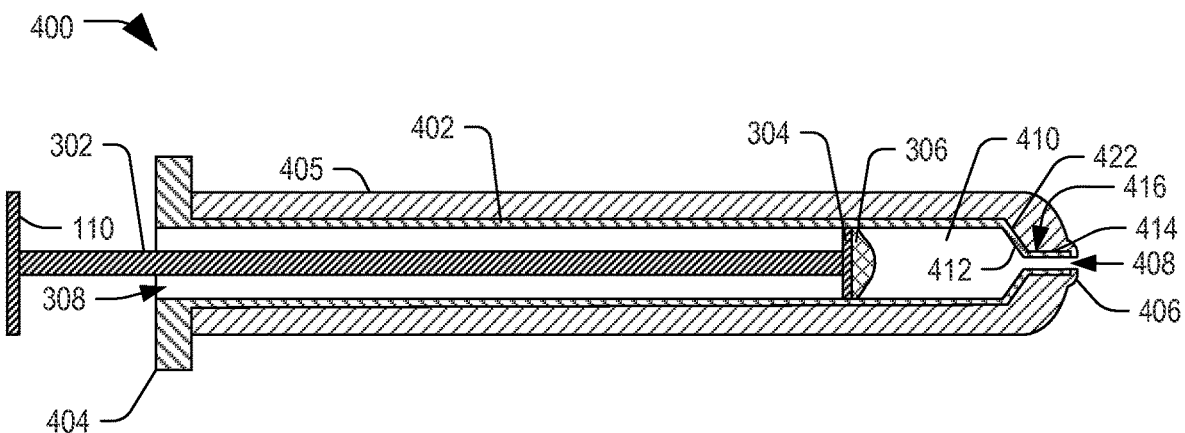
FIG. 4 is a cross-sectional view of an apparatus including a syringe and a sheath including a nub, in accordance with certain embodiments of the present disclosure.

FIG. 4 is a cross-sectional view of an apparatus 400 including a syringe 402 and a sheath 405 including a nub 406 according to some embodiments. The syringe 402 may include a body portion defining the cavity 308 sized to receive a plunger 110 having a rod portion and an end portion 304 that is coupled to a gasket or seal 306. The syringe 402 may further include a flange 404, a hub portion 412, and a nose portion.

414. The nose portion 414 may define an opening for fluid passage from a fluid area 410 and the external environment.
[0049] The sheath 405 may include a stop portion 422 configured to contact the hub portion 212 of the syringe 402 to seat the syringe 402 within the sheath 405. The sheath may be a substantially cylindrical (or tubular member) defining a cavity sized to receive the syringe 402. The sheath 405 may also include an opening 416 configured to receive the neck portion 414 of the syringe 402. The sheath 405 may further may include a nub 406 that extends outward from a distal end of the sheath 405. The nub 406 may have a rounded, substantially hemispherical, ring, elliptical, or other rounded shape that may partially define the opening 416 that is configured to align with a corresponding opening 108 through the neck portion 414 to allow fluid passage.

In some embodiments, the sheath 405 may be formed from a first material, and the syringe 402 may be formed from a second material. The first material may be more elastic, more malleable, softer, or any combination thereof relative to the second material. In some embodiments, the sheath 405 may have a substantially cylindrical shape without edges and may define an opening on a proximal end that is sized to receive a syringe 402. The sheath 405 may include one or more openings configured to align with an opening on the syringe. Further, in some embodiments, the surface of the sheath 405 may have some texture or uneven areas. Additionally, in some embodiments, the sheath 405 may include an attachment element, such as threads to mate with corresponding threads on an outer surface of a syringe, a flange element configured to mate with a corresponding recess on the syringe, some other attachment structure, or any combination thereof. An example of a sheath that may include an attachment structure is described below with respect to FIG. 5.

Figure 5:
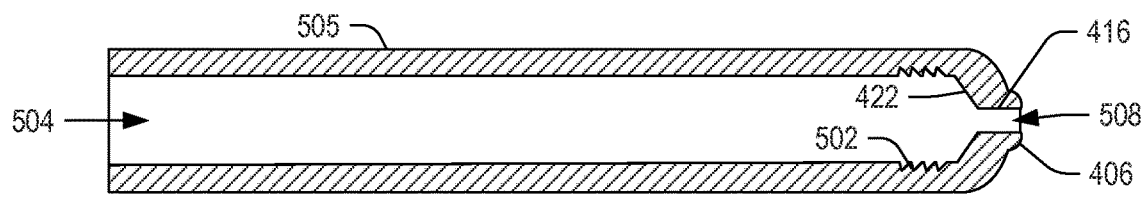
FIG. 5 is a cross-sectional view of a sheath including a nub and a threaded attachment, in accordance with certain embodiments of the present disclosure.

FIG. 5 is a cross-sectional view 500 of a sheath 505 including a nub 406 and a threaded attachment 502 according to some embodiments. The sheath 505 may define a cavity 504 sized to receive a syringe and may include an opening 508 configured to align to a corresponding opening 408 of a syringe. The sheath 505 further may include an attachment feature 502. In the illustrated example, the attachment feature 502 may be threads configured to fit corresponding threads on an exterior surface of the syringe. The user may turn the syringe within the cavity 504 in order to secure the sheath 505 to the syringe.

In some embodiments, the size of the opening 416 may be sufficiently narrow to apply a hoop stress on the neck portion 414 of the syringe 402 to secure the sheath 505 to the syringe. In some embodiments, an extension on an inner surface of the sheath 505 may be configured to mate with a corresponding recess on an exterior surface of the syringe to secure the sheath 505 to the syringe.

In some embodiments, the sheath 505 may be formed from a medical grade silicone. In some embodiments, the sheath 505 may be formed from a medical device material, such as a polymer designed to support medical applications and to maintain its material properties even after sterilization. In some embodiments, the sheath 505 may be formed from a flexible, substantially malleable material that may be of a different material from that of the syringe.

Figure 6:
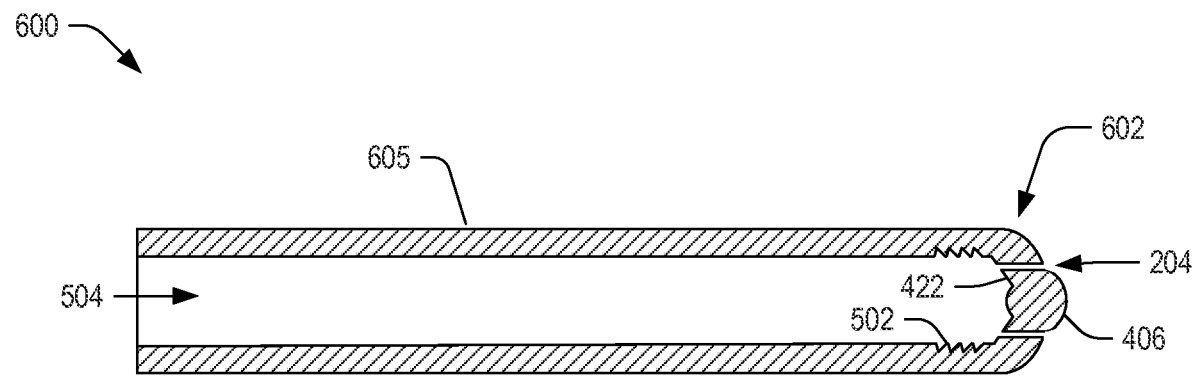
FIG. 6 is a cross-sectional view of a sheath including a nub and a threaded attachment, in accordance with certain embodiments of the present disclosure.

FIG. 6 is a cross-sectional view 600 of a sheath 605 including a nub 406 and a threaded attachment 502 according to some embodiments. The sheath 605 defines a cavity 504 sized to receive a syringe and may include a threaded feature 502 configured to mate with a corresponding feature on an outside surface of the syringe to secure the syringe within the sheath 605. The sheath 605 may include a nub 406 that extends from a distal end 602 of the sheath 605. The sheath 605 may include openings 204 about a periphery of the nub 406.

Figure 7:
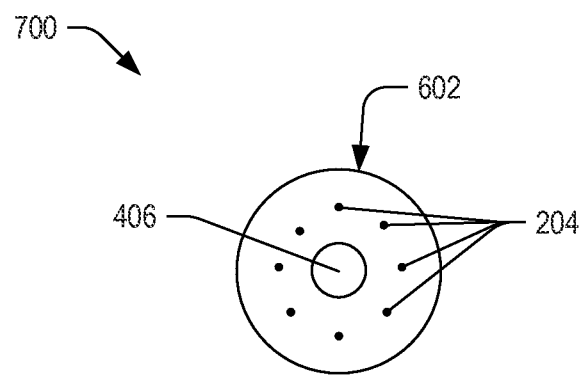
FIG. 7 is a front view of a distal end of the sheath of FIG. 6, in accordance with certain embodiments of the present disclosure.

FIG. 7 is a front view 700 of a distal end 602 of the sheath 605 of FIG. 6 according to some embodiments. The distal end 602 may include openings 204 and nub 406. While the openings 204 are distributed around the nub 406 of the distal end 602 approximately midway between the nub 406 and the peripheral edge of the distal end 602, in some embodiments, the openings 204 may be positioned closer to the peripheral edge or closer to the nub 406. Further, in some embodiments, additional openings or fewer openings may be provided. One possible example of a distal end that may include an additional opening is described below with respect to FIG. 8.

Figure 8:
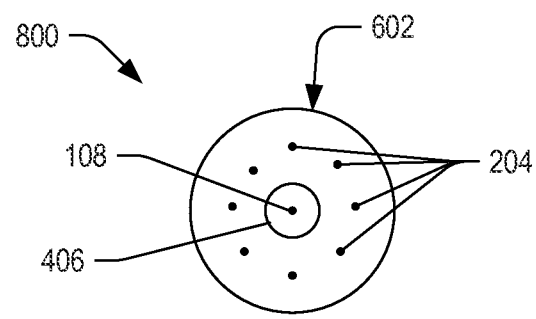
FIG. 8 is a front view of a distal end of a sheath, similar to the sheath of FIG. 6, in accordance with certain embodiments of the present disclosure.

FIG. 8 is a front view 800 of a distal end 602 of a sheath, similar to the sheath 605 of FIG. 6, according to some embodiments. The front view 800 may include the opening 108 that extends through a center of the nub 406 in addition to the openings 204.

In some embodiments, the nub 406 may be positioned at approximately a center of the distal end 602. In some embodiments, the nub 406 may be offset from a center of the distal end 602. The opening 108 may be aligned to a longitudinal axis of a syringe.

Figure 9:
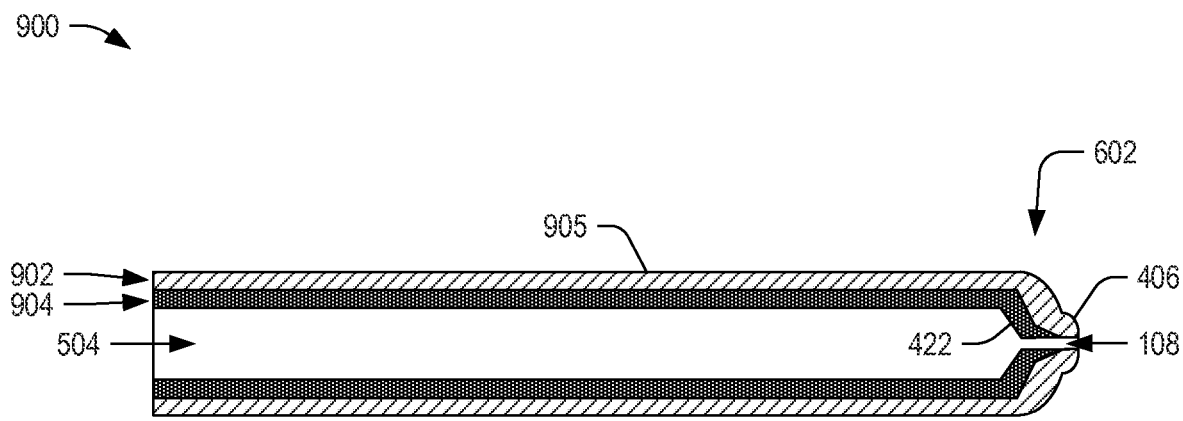
FIG. 9 is a cross-sectional view of a sheath including a nub, in accordance with certain embodiments of the present disclosure.

FIG. 9 is a cross-sectional view 900 of a sheath 905 including a nub 406 according to some embodiments. The sheath 905 may include multiple layers including an outer layer 902 and an inner layer 904. The sheath 905 may define an opening 504 sized to receive a syringe. The outer layer 902 may include the nub 406. In some embodiments, the inner layer 904 and the outer layer 902 may cooperate to form the nub 406. In some embodiments, the inner layer 904 may be formed from a first material and the outer layer 902 may be formed form a second material. In some embodiments, the first material may be more rigid than the second material. [0059] While the illustrated example of FIG. 9 depicts the inner layer extending from the opening of the proximal end along its entire length to the opening of the distal end 602, in some embodiments, the inner layer may extend only a portion of the length of the sheath 905. One possible example of a sheath having an inner layer that extends for only a portion of the length of the sheath is described below with respect to FIG. 10.

Figure 10:
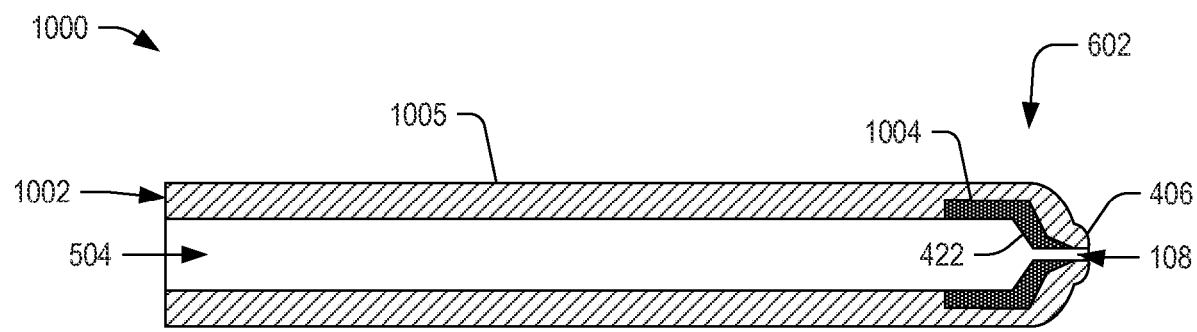
FIG. 10 is a cross-sectional view of a sheath including a nub, in accordance with certain embodiments of the present disclosure.

FIG. 10 is a cross-sectional view 1000 of a sheath 1005 including a nub 406 according to some embodiments. The sheath 1005 may include multiple layers including a first layer 1002 that extends about an entire periphery of the sheath 1005. The sheath 1005 may further include an inner layer 1004 that extends over a portion of an interior surface of the sheath 1005. In some embodiments, the inner layer 1004 may extend over the stop portion 422 of the sheath 1005, providing a relatively rigid seat against which the syringe may be positioned without over-stressing the distal end 602 of the sheath 1005.

In some embodiments, the nub 406 may include an opening that extends therethrough, and the nub 406 may be positioned at approximately a center of the distal end 602. In some embodiments, the nub 406 may be offset from a center axis of the sheath 1005. In some embodiments, the nub 406 may extend at least partially over the opening 108 to prevent the fluid from dispensing in a direct stream out of the opening 108, and dispersing the fluid over a larger spray area than a fluid stream would otherwise provide.

While the embodiments described above included a syringe with a nub and a sheath with a nub, in some embodiments, the nub may be provided on a cap configured to fit onto a distal end of a syringe. Examples of such embodiments are described below with respect to FIGS. 11-14.

Figure 11:
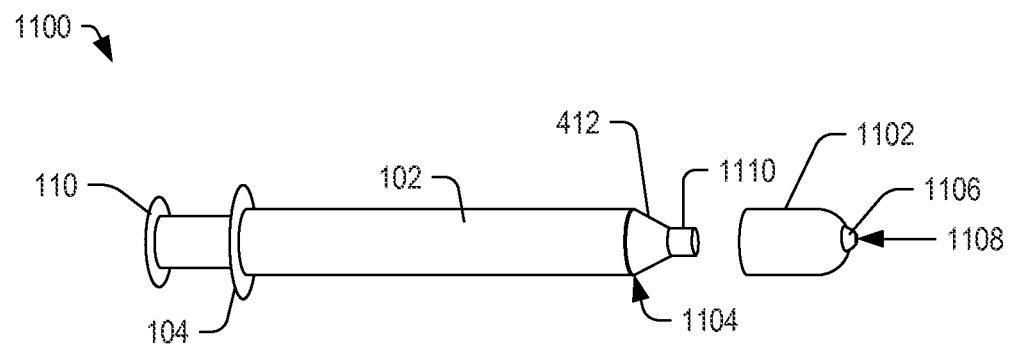
FIG. 11 is a side view of an apparatus including a syringe and a cap including a nub, in accordance with certain embodiments of the present disclosure.

FIG. 11 is a side view of an apparatus 1100 including a syringe 102 and a cap 1102 including a nub 1106 according to some embodiments. The syringe 102 may include the plunger 110 and the flange 104. The syringe 102 may further include a hub portion 412 and a neck portion 1110 that extends from the hub portion 412 and through which the opening 108 may extend. The syringe 104 may further include an attachment feature 1104 configured to mate with a corresponding attachment feature of the cap 1102.

In some embodiments, the cap 1102 may be a substantially cylindrical shape (or tubular shape) having a rounded end that may include a nub 1106 and an opening 1108 that extends through the cap 1102. The cap 1102 may include an attachment feature on an interior surface of the cap 1102 that may be configured to couple to the attachment feature 1104 on the syringe 102 to secure the cap 1102 to the syringe 102. In some embodiments, the cap 1102 may include an opening 1108 configured to align to the opening 108 of the neck 1110 of the syringe 102.

Figure 12:
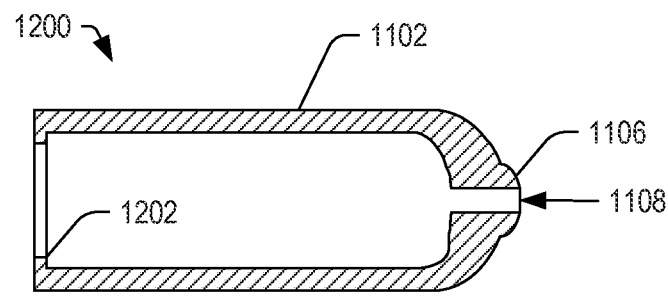
FIG. 12 is a cross-sectional view of the cap of FIG. 11 including an attachment mechanism, in accordance with certain embodiments of the present disclosure.

FIG. 12 is a cross-sectional view 1200 of the cap 1102 of FIG. 11 including an attachment mechanism 1202 according to some embodiments. The attachment mechanism 1202 may be configured to mate with a corresponding recess 1104 of the syringe 102 in a manner that may be similar to a pen cap coupling to a pen. In some embodiments, the attachment feature 1202 may be a flange or other structure that extends from an inner surface of the cap 1102. In some embodiments, the attachment feature 1202 may extend about an entire inner circumference of the cap 1102. In some embodiments, the attachment feature 1202 may extend about a portion of the inner circumference of the cap 1102.

Figure 13:
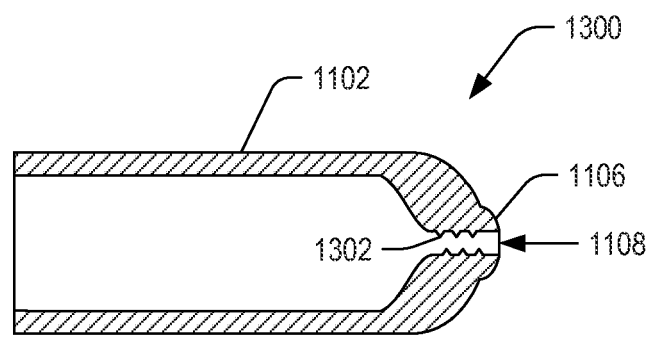
FIG. 13 is a cross-sectional view of the cap of FIG. 11 including an attachment mechanism, in accordance with certain embodiments of the present disclosure.

FIG. 13 is a cross-sectional view 1300 of the cap 1102 of FIG. 11 including an attachment mechanism 1302 according to some embodiments. In some embodiments, the attachment mechanism 1302 may be located at a stop portion of the cap 1102. In some embodiments, the attachment mechanism 1302 may be located within an opening 1108 of the cap 1102. The attachment mechanism 1302 may be a threaded portion configured to mate with a corresponding threaded portion of a syringe to secure the cap 1102 to the syringe.

While the cap 1102 depicted in FIGS. 11-13 may include the opening 1108 located at a center of the rounded end of the cap 1102, it should be appreciated that, in some embodiments, the opening 1108 may be offset from a center axis of the cap 1102. In some embodiments, the cap 1102 may include multiple openings as described below with respect to FIG. 14.

Figure 14:
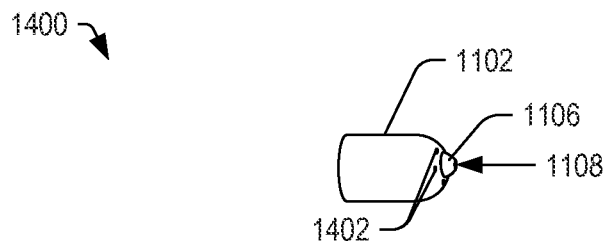
FIG. 14 is a side view of a cap configured to couple to a syringe, in accordance with certain embodiments of the present disclosure.

FIG. 14 is a side view 1400 of a cap 1102 configured to couple to a syringe according to some embodiments. The cap 1102 may include a nub 1106 and an opening 1108 that extends through the nub 1106. Additionally, the cap 1102 may include multiple openings 1402, which may be arranged circumferentially about the nub 1106. Within the cap 1102, the openings 1402 may be coupled to an opening 108 of the syringe by conduits extending from the opening 108 to the openings 1402.

Figure 15:
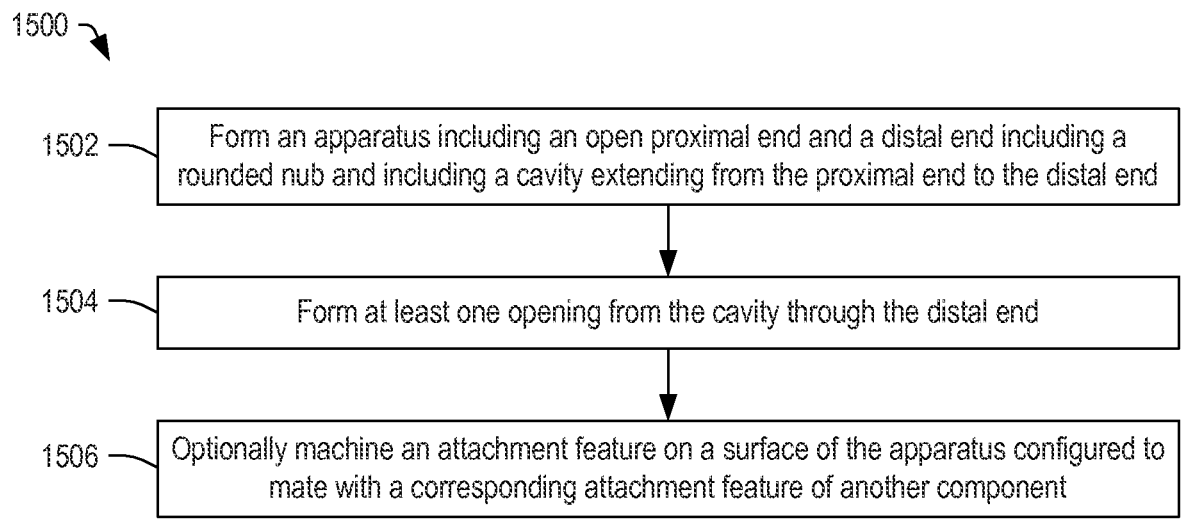
FIG. 15 is a flow diagram of a method of forming a sheath configured to receive a syringe, in accordance with certain embodiments of the present disclosure.

FIG. 15 is a flow diagram of a method 1500 of forming a sheath configured to receive a syringe according to some embodiments. At 1502, an apparatus may be formed that may include an open proximal end and a distal end including a rounded nub and that may include a cavity extending from the proximal end to the distal end. Advancing to 1504, at least one opening is formed that extends from the cavity through the distal end. Continuing to 1506, an attachment feature may be optionally machined on a surface of the apparatus configured to mate with a corresponding attachment feature of another component. In some embodiments, the apparatus may be a syringe having a nub, and the attachment feature may include a recess configured to mate with a flange or ridge on an interior surface of a cap or sheath (the other component) that also may include a nub. In some embodiments, the apparatus may be a sheath or cap that is configured to couple to a corresponding attachment feature on a syringe. In some embodiments, the sheath and the syringe may include a nub. In some embodiments, the sheath may include a nub, and the syringe may include a neck portion that extends at least partially toward the nub.

Figure 16A:
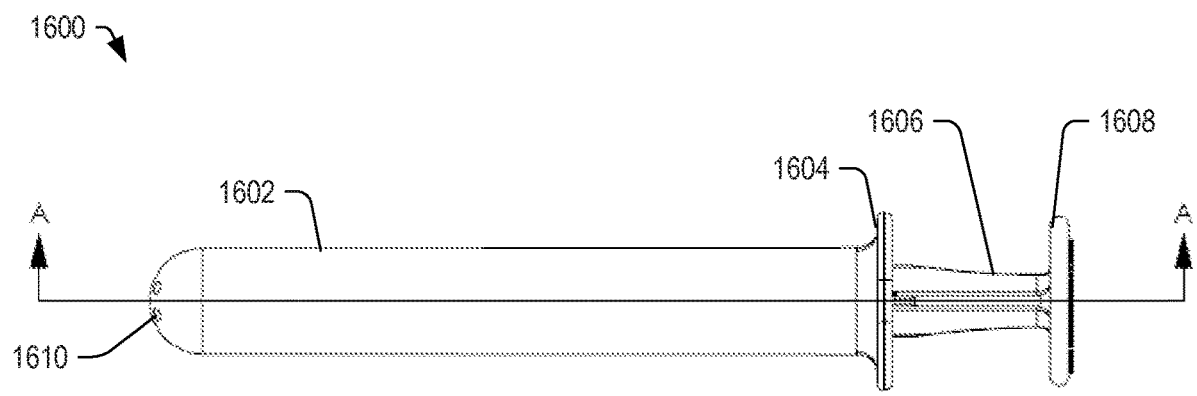
FIG. 16A is a side-view of a syringe including multiple openings, in accordance with certain embodiments of the present disclosure.

FIG. 16A is a side-view of a syringe 1600 including multiple openings, in accordance with certain embodiments of the present disclosure. The syringe 1600 may include a body portion 1602 having a flange 1604. The body portion 1602 may define a cavity sized to receive a rode portion 1606 of a plunger 1608. The body portion 1602 may further include one or more openings 1610 at a distal end opposite the flange 1604. The one or more openings 1610 may extend from an exterior surface through the distal end of the body portion and into the internal cavity. In some embodiments, the number, the spacing, the shape, and the interior dimensions of the openings 1610 may vary to provide a desired diffusion for fluid disbursed through the openings 1610.

Figure 16B:
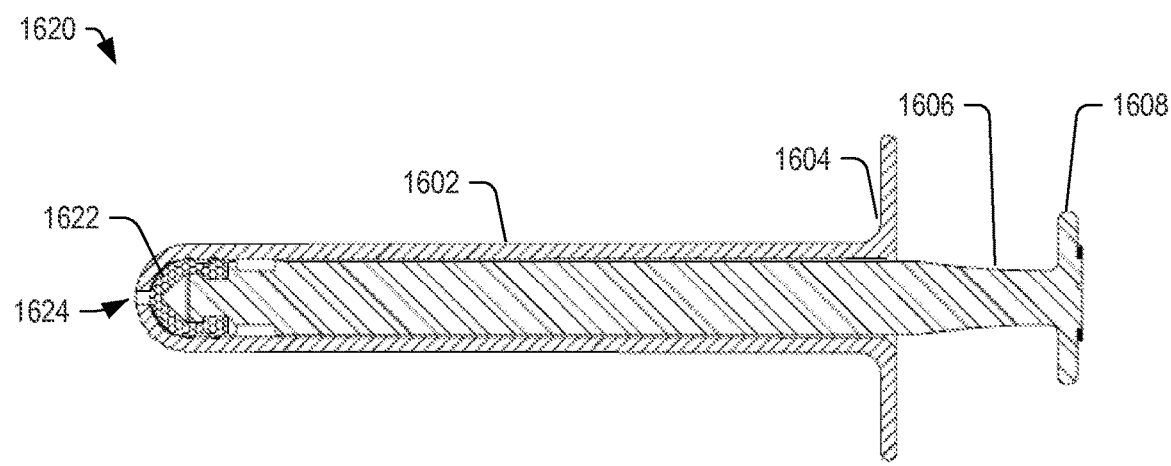
FIG. 16B is a cross-sectional view of the syringe of FIG. 16A taken along line A-A, in accordance with certain embodiments of the present disclosure.

FIG. 16B is a cross-sectional view 1620 of the syringe 1600 of FIG. 16A taken along line A-A, in accordance with certain embodiments of the present disclosure. The syringe 1600 further includes a seal 1622 configured to fit over a tip of the rod portion 1606 of the plunger 1608 to form a fluid seal against the interior surface of the cavity of the body portion 1602 in order to push fluid toward and through the openings 1610. In the cross-sectional view, a central opening 1624 is shown, which may be formed at a substantially central position in the distal end of the body portion 1602 (opposite end from the flange 1604).

Figure 17:
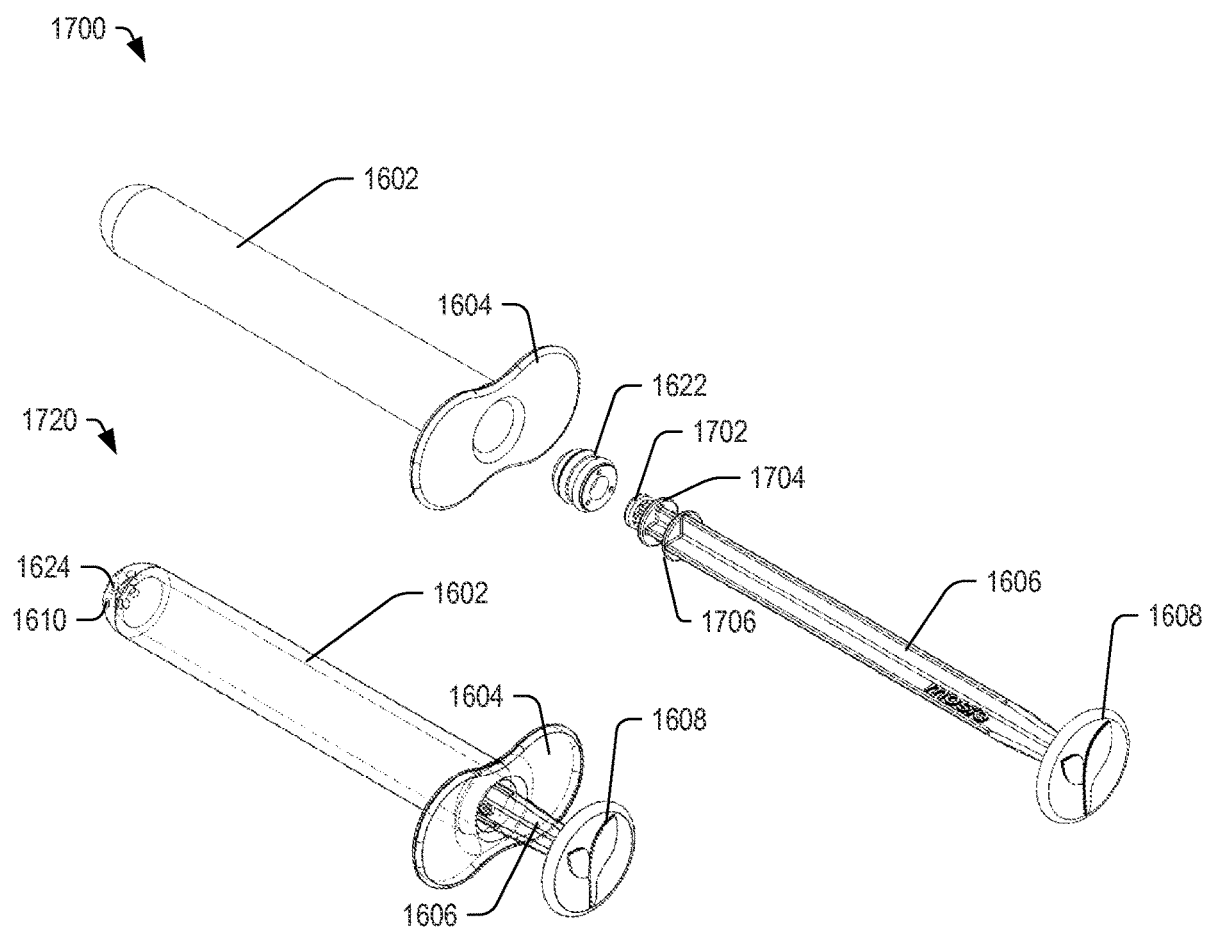
FIG. 17 is an exploded view and a perspective view of the syringe of FIG. 16A, in accordance with certain embodiments of the present disclosure.

FIG. 17 is an exploded view 1700 and a perspective view 1720 of the syringe 1600 of FIG. 16A, in accordance with certain embodiments of the present disclosure. The exploded view 1700 includes the seal 1622. Further, the exploded view 1700 includes the rod portion 1606 of the plunger 1608. The rod portion 1606 includes an end 1702 sized to fit into an opening of the seal 1622. The rod portion 1606 may further include a flange portion 1702 sized to engage an interior surface of the seal 1622 and may further include a stopper portion 1704 configured to engage a portion of the seal 1622 to prevent over stressing. In some embodiments, the seal 1622 may be installed onto the end 1702 and may be pushed over the flange portion 1702 to engage the stopper portion 1704. The flange portion 1702 may engage an interior portion of the seal 1622 to secure the seal 1622 to the rod portion 1606.

Figure 18A:
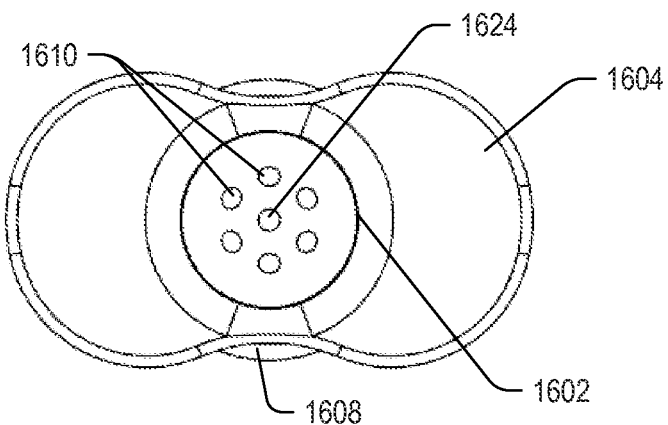
FIG. 18A is a front view of the syringe of FIG. 16A, in accordance with certain embodiments of the present disclosure.

FIG. 18A is a front view 1800 of the syringe 1600 of FIG. 16A, in accordance with certain embodiments of the present disclosure. The front view 1800 depicts the plunger 1608, the flange 1604, and the body portion 1602. The body portion 1602 includes the openings 1610 and the central opening 1624. In the illustrated example, the openings 1610 and 1624 are approximately the same size and shape. How-ever, in other embodiments, the openings 1610 may be a different size and shape as compared to the central opening 1624. In some embodiments, instead of being arranged in a circular formation around the central opening 1624, the openings 1624 may be arranged in a different configuration.

Figure 18B:
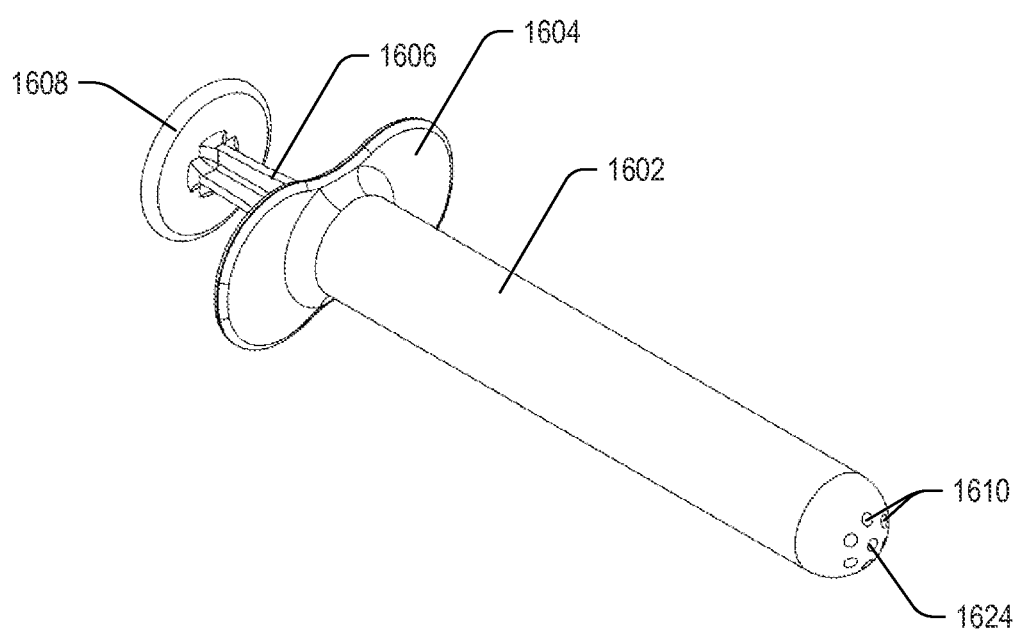
FIG. 18B is a perspective view of the syringe of FIG. 16A, in accordance with certain embodiments of the present disclosure.

FIG. 18B is a perspective view 1820 of the syringe 1600 of FIG. 16A, in accordance with certain embodiments of the present disclosure. The perspective view 1820 includes the openings 1610 and 1624 at the distal end of the body portion 1602 opposite to the flange 1604.

Figure 19A:
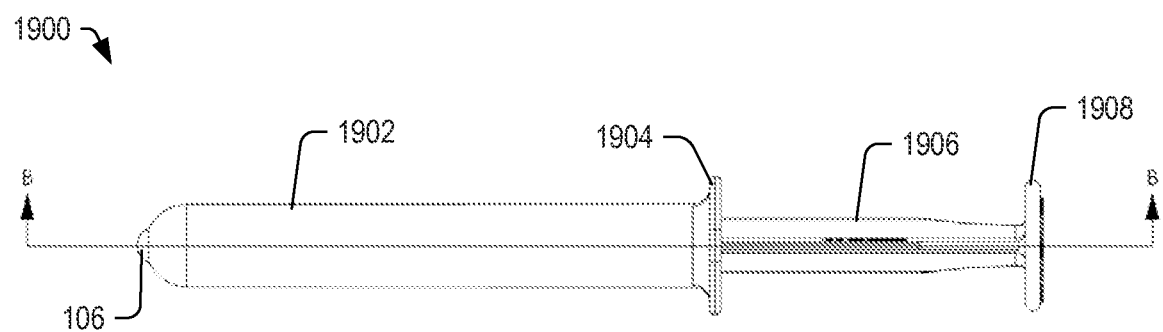
FIG. 19A is a side view of a syringe including a nub, in accordance with certain embodiments of the present disclosure.

FIG. 19A is a side view of a syringe 1900 including a nub 106, in accordance with certain embodiments of the present disclosure. The syringe 1900 may include a body portion 1902 having a flange 1904. The syringe 1900 may further include a plunger 1908 having a rod portion 1906, which may have an end to which a seal 1922 may be coupled. The syringe 1900 may include an opening that may extend from an exterior surface of the nub 106 into the interior cavity defined by the body portion 1902.

In some embodiments, the opening through the nub 106 may have a substantially irregular shape, which may diffuse or otherwise distribute fluid as it passes through the opening. Examples of such irregular shapes may be described below with respect to FIGS. 20A-22B. As used herein, the term "irregular shape" refers to a shape other than a circle or square shape.

Figure 19B:
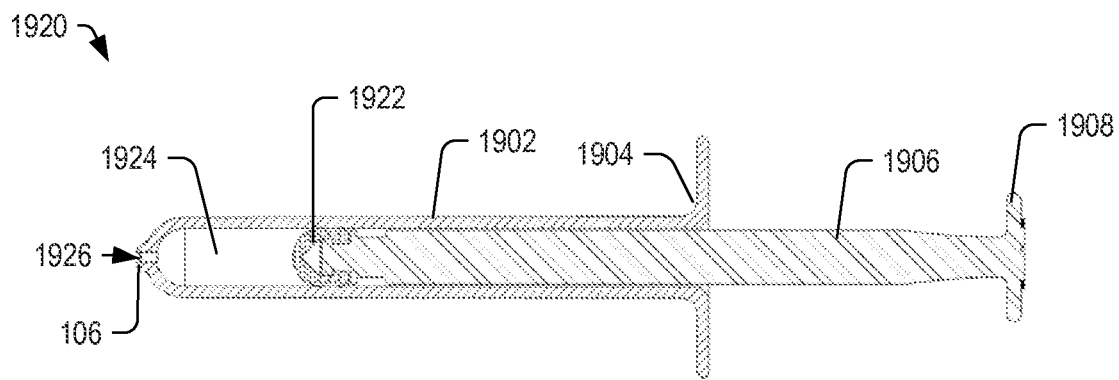
FIG. 19B is cross-sectional view of the syringe of FIG. 19A taken along line B-B, in accordance with certain embodiments of the present disclosure.

FIG. 19B is cross-sectional view 1920 of the syringe 1900 of FIG. 19A taken along line B-B, in accordance with certain embodiments of the present disclosure. The cross-sectional view 1920 depicts a cavity 1924 within the body portion 1902. The cavity 1924 may hold fluid to be disseminated through the opening 1926, which may extend from the cavity 1924 through the nub 106.

As discussed above, in some embodiments, the body portion 1902 may include a plurality of openings. In some embodiments, the opening 1926 may have a substantially irregular shape. Further, in some embodiments, the opening 1926 may define a fluid passage having an irregular internal shape. Examples of the irregular shaped opening 1926 may be described below with respect to FIGS. 20A-21D.

Figure 20A:
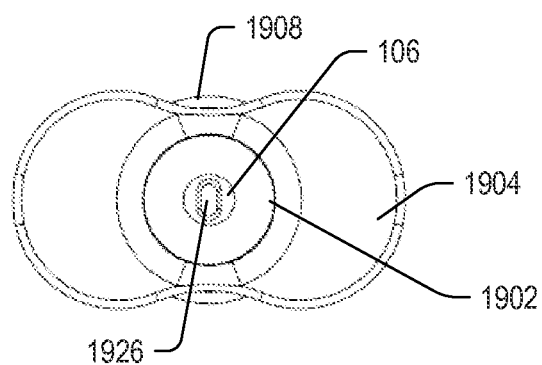
FIG. 20A is a front view of the syringe of FIG. 19A, in accordance with certain embodiments of the present disclosure.

FIG. 20A is a front view 2000 of the syringe 1900 of FIG. 19A, in accordance with certain embodiments of the present disclosure. The front view 2000 includes the body portion 1902, the flange 1904, the plunger 1908 and the nub 106. In the illustrated embodiment, the opening 1926 may be implemented as a rounded rectangular shape, an elliptical shape, an oval shape, or another non-circular shape. The opening 1926 may extend from the cavity within the body portion 1902 through the nub 106. Other openings may also be provided (either through or around the nub 106).

Figure 20B:
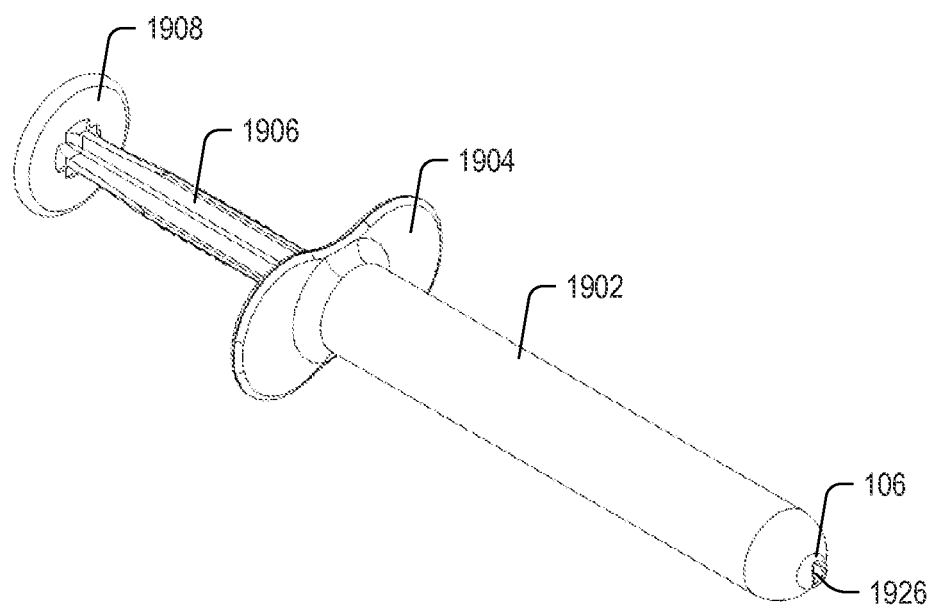
FIG. 20B is a perspective view of the syringe of FIG. 19A, in accordance with certain embodiments of the present disclosure.

FIG. 20B is a perspective view 2020 of the syringe 1900 of FIG. 19A, in accordance with certain embodiments of the present disclosure. The perspective view 2020 depicts the opening 1926 having a substantially elliptical, oval or oblong shape, which may provide a diffused fluid dispersion pattern as compared to a high pressure stream that might be produced by a small circular opening.

Figure 21A:
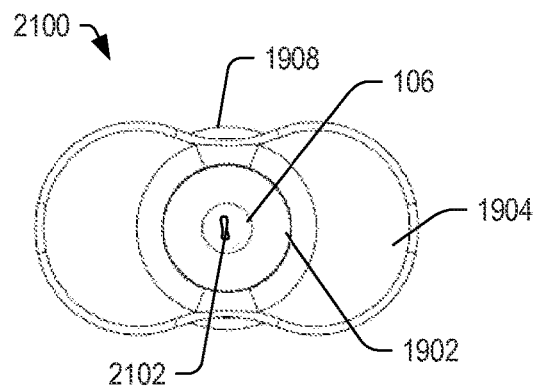
FIGS. 21A-21D are front views of the syringe of FIG. 19A, in accordance with certain embodiments of the present disclosure.

FIGS. 21A-21D are front views of the syringe of FIG. 19A, in accordance with certain embodiments of the present disclosure. Referring now to FIG. 21A, a front view 2100 of the syringe 1900 of FIG. 19A is shown. The front view 2100 includes the body portion 1902, the flange 1904, the plunger 1908 and the nub 106. The nub 106 may include an opening 2102 having an irregular shape, such as a barbell type of shape or another shape.

Figure 21B:
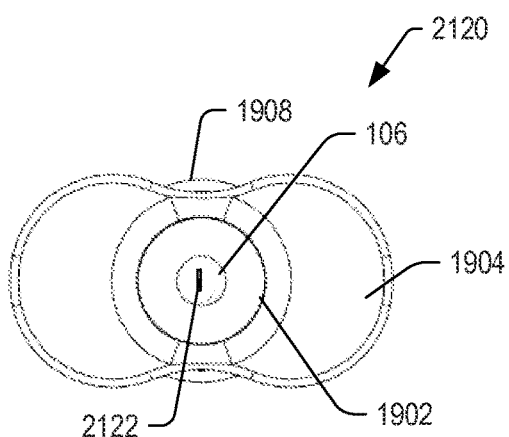

FIG. 21B depicts a front view 2120 of the syringe 1900 of FIG. 19A including an opening 2122 having an irregular shape that is substantially rectangular-shaped. In some embodiments, the rectangular-shaped opening 2122 may provide a non-uniform dispersal of fluid.

Figure 21C:
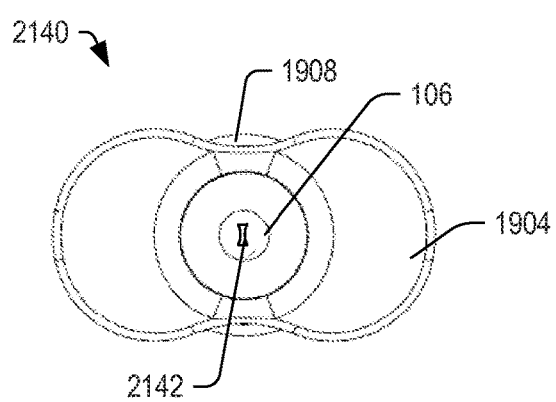

FIG. 21C depicts a front view 2140 of the syringe 1900 of FIG. 19A including an opening 2142 having an irregular shape that is substantially hourglass-shaped. In some embodiments, the hourglass-shaped opening 2142 may provide a non-uniform dispersal of fluid.

Figure 21D:
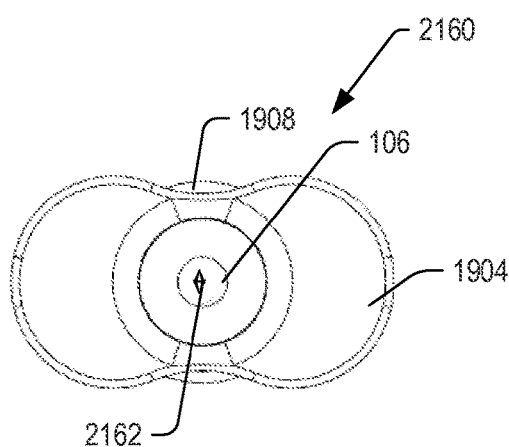

FIG. 21D depicts a front view 2160 of the syringe 1900 of FIG. 19A including an opening 2162 having an irregular shape that is substantially diamond-shaped. In some embodiments, the diamond-shaped opening 2162 may provide a non-uniform dispersal of fluid.

FIG. 22A is a cross-sectional view 2200 of the syringe 1900 of FIG. 19A including an opening 2204. In some embodiments, the opening 2204 may define a cylindrically-shaped fluid passage extending from the cavity within the body portion 1902 through the nub 106. The cross-sectional view 2200 further depicts the rod portion 1906 of the plunger 1908 extending within the cavity of the body portion 1902. Further, the rod portion 1906 may include an end portion 2222, a flange portion 2224, and a stop portion 2226. Further, a seal 2202 may be coupled to the end portion 2222 and may be configured to provide a fluid seal extending a full internal diameter of the cavity to push fluid toward the opening as the plunger 1908 is pushed toward the distal end of the body portion 1902.

FIG. 22B is a cross-sectional view 2220 of a portion of the syringe 1900 including the opening 2204 having a substantially cylindrical fluid passage that extends from an external surface of the nub 106 to a cavity defined by the hub portion of the syringe 1900. In the illustrated example, the rod portion 1906 is fully inserted within the cavity such that the seal 2202 is in contact with the interior surface of the distal end of the body portion 1902.

FIG. 22C is a cross-sectional view 2240 of a portion of the syringe 1900 including an opening 2242 defining a fluid passage having a varying internal diameter. In the illustrated example, the varying internal diameter may form a Venturi tube type of passage having a narrow portion toward the middle of the passage and a wider portion at the opening to provide reduced pressure and increased dispersion.

FIG. 22D is a cross-sectional view 2260 of a portion of the syringe 1900 including an opening 2262 defining a fluid passage. Within the opening 2262, the syringe 1900 may include an obstruction element 2264 configured to diffuse or otherwise disperse fluid that may be pushed through the opening 2262 by the plunger 1908 via the rod portion 1906 and the seal 2202.

Figure 23:
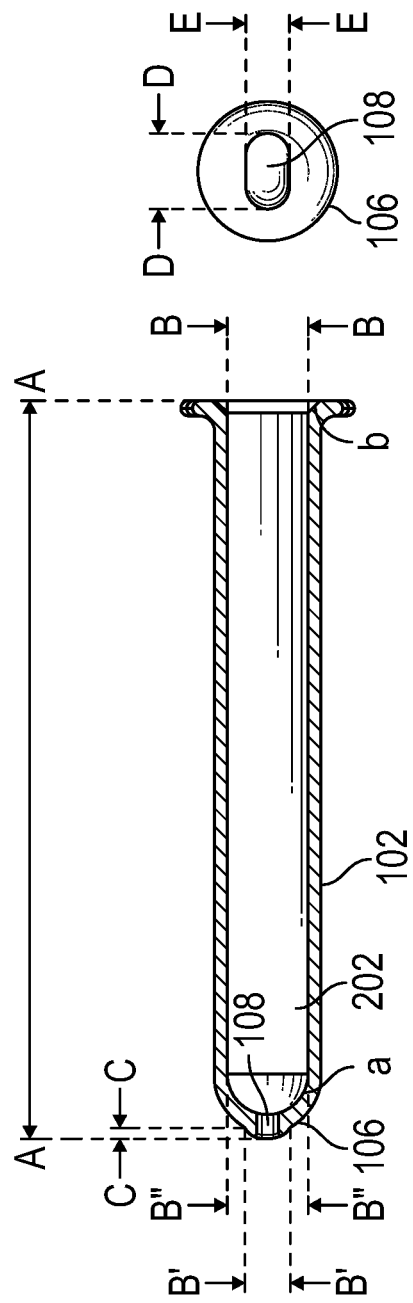
FIG. 23 is a side cross-sectional view of the syringe with sectional lines and a front view of the syringe with sectional lines.

FIG. 23 is a side view cross-sectional view and front view with sectional lines illustrating preferred dimensional measurements of the present syringe assembly. Section A-A is the length of syringe 102. Section B-B is the height or width of the syringe. Section B"-B" is the is the internal diameter of the syringe barrel 202. Section B'-B' is the exterior diameter of the nub 106. Section C-C is the height of the nub 106. Attention is directed in particular to the nub 106. The form of nub 106 is subtle, with smooth curves to facilitate comfortable insertion. Nub 106 is small relative to the length of barrel 202 from which it is form. In an exemplary preferred embodiment, the length of barrel 202, including nub 106, of section A-A is 3.6 inches (91.4 mm) whereas the length C-C (that is, the height of the nub portion 106 which extends contiguously from the end of barrel 202), is approximately 0.2 inches (4.9 mm) or in a range of 4 mm-6 mm. The length/height of Nub 106, therefore, is approximately 5.4% the length of barrel 202. An operable preferred embodiment has a nub height in the range of 4% to 6% the length of the barrel. In the same exemplary preferred embodiment, the diameter of nub B'-B' has a nub exterior diameter in the range of 0.3 to 0.4 inches (7.6 mm-10.1 mm.

Opening 108 traversing through nub 106 and has preferred dimensions of 0.09 inches (2.3 mm) by 0.05 inches (1.3 mm).

The relatively small size, dimensions, and smooth curvature of nub 106 and the preferred dimensions of the opening 108 are not purely ornamental, arbitrary or merely a matter of design choice. The embodiment of the preferred dimensions is the result of testing, iteration and refining of the design with the objective of obtaining desired performance characteristics. The performance characteristics include little loss of payload in delivery to the cervix, effective dispersal of the payload, and comfort of use. The small nub is comfortable for the user and provides a very short channel or reservoir in the opening through which the payload is delivered, resulting in very little loss of payload left trapped in the syringe, and a geometry of the opening to provide effective dispersal of the payload into the cervix.

Nevertheless, In some embodiments, the invention contemplates that the shape of the opening, the shape of the fluid passage, or any combination thereof may be selected to provide a desired fluid dispersion at a distal end of the syringe. In some embodiments, the external diameter and length of the syringe may be selected to provide a suitable insertion vessel through which the fluid may be presented. With the use of an insemination syringe, for example, the vagina extends from the vulva to the uterus, and the length of the vagina may vary from about 2.75 inches to about 4.75 inches. Accordingly, the length of the syringe may be selected to be a suitable length for a particular woman. For insemination purposes, the body portion of the syringe (from the distal end to the flange) may be approximately 2.75 to 3 inches in length. Other lengths may also be possible.

In conjunction with FIGS. 1-23, an apparatus is described that may include a sheath or body portion having a distal end having a rounded nub and at least one opening. In some embodiments, the at least one opening may include a non-circular or irregular shaped opening, such as a slit, an hourglass shape, a barbell shape, a diamond shape, another shape, or any combination thereof. The distal end of the apparatus may be rounded to present a blunt or "edgeless" end presenting a substantially smooth transition from an elongate portion to a distal portion of the apparatus. In some embodiments, the apparatus may be used for home-based artificial insemination, such as by insertion of the apparatus into the vagina of a woman until the nub contacts the woman's cervix. The plunger may then be depressed to expel seminal fluid onto the cervix through the opening to provide artificial insemination.

In some embodiments, the apparatus may include a syringe having a substantially tubular shape and having a substantially rounded distal end. The syringe may further include a rounded nub extending from the distal end proximate to a longitudinal axis of the syringe. In some embodiments, the rounded nub may include the opening to allow fluid to pass therethrough. In some embodiments, the distal end may include a plurality of openings to allow fluid passage. In some embodiments, the opening or openings in the rounded nub, the other openings at the distal end, or any combination thereof may have non-circular or irregular shapes to diffuse the fluid as it passes through the one or more openings.

In some embodiments, the apparatus may include a syringe and a sheath having a cavity sized to receive the syringe. The sheath may include one or more openings on a distal end that are configured to align with (or mate with) a fluid opening of the syringe. In some embodiments, the sheath may include an attachment feature configured to mate with a corresponding feature on the syringe. In an example, the attachment feature may include threads configured to mate with corresponding threads of the syringe to secure the syringe within the sheath. In another example, the attachment mechanism may include a raised edge on one of an interior surface of the sheath and an exterior surface of the syringe that is configured to mate with a corresponding recess on the other of the exterior surface of the syringe and the interior surface of the sheath. Further, in some embodiments, at least a portion of the sheath may be formed from a first material, and at least a portion of the syringe may be formed from a second material. In some embodiments, the first material may be more flexible or malleable than the second material.

In some embodiments, a cap or partial sheath may be configured to mate with a syringe to provide a rounded end having a nub and including one or more openings for fluid passage. In some embodiments, the nub may be rounded and may include an opening configured to align to an opening of the syringe to allow fluid from the syringe to pass therethrough. The opening of the cap or partial sheath may be irregular in shape (e.g., oval, elliptical, hourglass shaped, barbell shaped, rectangular shaped, or some other shape). In some embodiments, the cap or partial sheath may include an attachment feature configured to mate with a corresponding feature of the syringe to secure the cap or partial sheath to the syringe. In some embodiments, the syringe may be formed from a first material, and the cap or partial sheath may be formed from a second material. The first material may be more rigid than the second material.

Although the present invention has been described with reference to preferred embodiments, workers skilled in the art will recognize that changes may be made in form and detail without departing from the scope of the invention.

What is claimed is:

1. An apparatus comprising:
a plunger; and
a substantially cylindrical body extending along a longitudinal axis located at a center of the cylindrical body, the cylindrical body configured to penetrate and extend into a vagina and including an end portion defining a distal end of the cylindrical body, the end portion having rounded edges and defining a cavity sized to receive the plunger, the substantially cylindrical body having a length and including an opening on the longitudinal axis and elongated across the longitudinal axis, the opening defining a fluid passage extending from the cavity to an external surface, the opening defining an outer extent at the distal end and at the external surface to dispense a fluid from the apparatus, and the opening having an elongated shape at the outer extent, the elongated shape configured to diffuse a fluid passing through the opening.

2. The apparatus of claim 1, wherein the elongated shape of the outer extent defines a slit, an oval shape, an elliptical shape, an hourglass shape, a rectangular shape, or a diamond shape.

3. The apparatus of claim 1, further comprising a nub extending from the end portion for a distance of approximately 4% to 6% of the length of the substantially cylindrical body, wherein the nub has a rounded end defining the external surface.

4. The apparatus of claim 3, wherein the nub is curved in cross-section and the opening extends through the nub.

5. The apparatus of claim 3, wherein the substantially cylindrical body and the nub may be formed from a unitary material.

6. The apparatus of claim 1, wherein the substantially cylindrical body includes a fastener element configured to mate to a corresponding feature of a cap.

7. An apparatus comprising:
a cylindrical body having a proximal end, a distal end, and an elongate portion extending therebetween along a longitudinal axis at a center of the cylindrical body, the distal end and at least a portion of the elongate portion configured to penetrate and extend into a vagina, the distal end having a rounded corner relative to the elongate portion to form a smooth transition from the elongate portion to the distal end, the distal end further including an opening on the longitudinal axis and defining a passage through the distal end, the opening defining an outer extent with an elongated shape across the longitudinal axis; and
a nub disposed on the distal end and extending a distance in a range of 4 mm to 6 mm from the distal end, the nub having a rounded end.

8. The apparatus of claim 7, wherein the elongated shape of the outer extent defines a slit, an oval shape, an elliptical shape, an hourglass shape, a rectangular shape, or a diamond shape, and wherein the shape is configured to diffuse a fluid passing through the opening.

9. The apparatus of claim 7, wherein the rounded end of the nub defines one of a substantially hemispherical shape, a substantially annular shape, or a substantially elliptical shape.

10. The apparatus of claim 7, wherein the nub includes the outer extent of the opening.

11. The apparatus of claim 10, wherein the body includes a first material and the nub includes a second material that is different from the first material.

12. The apparatus of claim 11, wherein the passage has a non-cylindrical shape.

13. The apparatus of claim 7, further comprising a plurality of second openings extending through the distal end of the body.

14. An apparatus comprising:
a tubular element including a body portion defining an internal cavity and having a distal end and a length along a longitudinal axis located at a center of the tubular element, at least a portion of the body portion and the distal end configured to penetrate and extend through a vagina, the distal end including a nub extending from the distal end approximately 4% to 6% of the body portion length and having an opening on the longitudinal axis with a non-circular shape across the longitudinal axis, the opening in fluid communication with the internal cavity via a fluid passage, the tubular element including a substantially smooth exterior surface having rounded edges adjacent the distal end; and
a plunger configured to fit within the cavity.

15. The apparatus of claim 14, wherein the non-circular shape defines a slit, an oval shape, an elliptical shape, an hourglass shape, a rectangular shape, or a diamond shape.

16. The apparatus of claim 14, wherein the tubular element defines a portion of a syringe.

* * * * *